United States Patent [19]

Tully

[11] 4,390,697
[45] Jun. 28, 1983

[54] PROCESS FOR THE PREPARATION OF TRIAZOLOQUINAZOLINONES

[75] Inventor: Wilfred R. Tully, Cirencester Glous, England

[73] Assignee: Roussel Uclaf, Paris, France

[21] Appl. No.: 317,858

[22] Filed: Nov. 3, 1981

[30] Foreign Application Priority Data

Nov. 10, 1980 [GB] United Kingdom ................. 8036025

[51] Int. Cl.³ ........................................... C07D 487/04
[52] U.S. Cl. .................................... 544/251; 544/115; 544/287
[58] Field of Search .............................. 544/115, 251

[56] References Cited

U.S. PATENT DOCUMENTS 3,053,844  9/1962  Miller et al. .................... 544/251 X

FOREIGN PATENT DOCUMENTS 2069495  8/1981  United Kingdom ................ 424/251

*Primary Examiner*—Donald G. Daus
*Assistant Examiner*—Diana G. Rivers
*Attorney, Agent, or Firm*—Hammond & Littell, Weissenberger and Muserlian

[57] ABSTRACT

A novel process for the preparation of triazoloquinazolinones of the formula

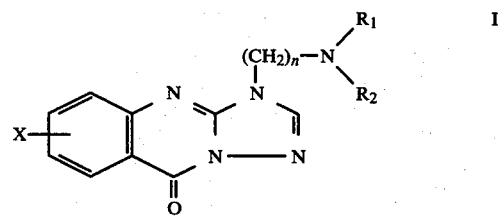

wherein X is selected from the group consisting of hydrogen, fluorine, chlorine, bromine, $-NO_2$, $-CF_3$, $-CH_3$ and $-OCH_3$, n is an integer from 2 to 5, $R_1$ and $R_2$ are individually selected from the group consisting of hydrogen, alkyl of 1 to 5 carbon atoms and hydroxyalkyl of 1 to 5 carbon atoms or taken together with the nitrogen atom which they are attached form a saturated heterocycle optionally containing another heteroatom and optionally substituted with at least one member of the group consisting of hydroxy, alkyl and hydroxy alkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms, aryl and aryl substituted with halogen or $-CF_3$ and their non-toxic, pharmaceutically acceptable acid addition salts having antihistaminic and bronchospasmolytic activity and novel intermediates.

9 Claims, No Drawings

4,390,697

1

PROCESS FOR THE PREPARATION OF TRIAZOLOQUINAZOLINONES

STATE OF THE ART

Commonly assigned U.S. patent application Ser. No. 234,544 filed Feb. 13, 1981, now U.S. Pat. No. 4,350,695 describes the compounds of formula I and their physiological activity and their use in the treatment of asthma, bronchitis and allergic disorders. The said application produces the compounds of formula I by reacting a compound of the formula

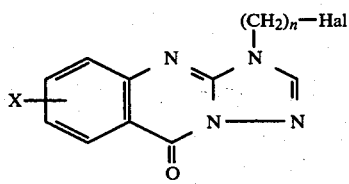

with an amine of the formula

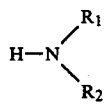

OBJECTS OF THE INVENTION

It is an object of the invention to provide a novel process for the preparation of the compounds of formula I and their non-toxic, pharmaceutically acceptable acid addition salts.

It is another object of the invention to provide novel intermediate compounds.

These and other objects and advantages of the invention will become obvious from the following detailed description.

THE INVENTION

The novel process of the invention for the preparation of the compounds of formula I and their acid addition salts

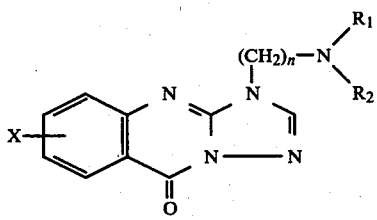

wherein X is selected from the group consisting of hydrogen, fluorine, chlorine, bromine, —NO$_2$, —CF$_3$, —CH$_3$ and —OCH$_3$, n is an integer from 2 to 5, R$_1$ and R$_2$ are individually selected from the group consisting of hydrogen, alkyl of 1 to 5 carbon atoms and hydroxyalkyl of 1 to 5 carbon atoms or taken together with the nitrogen atom which they are attached form a saturated heterocycle optionally containing another heteroatom and optionally substituted with at least one member of the group consisting of hydroxy, alkyl and hydroxyalkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms, aryl and aryl substituted with halogen or —CF$_3$, comprises reacting a compound of the formula

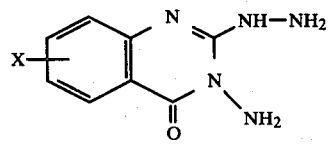

wherein X has the above definition with a compound of the formula

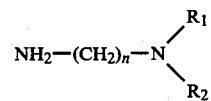

wherein R$_1$, R$_2$ and n have the above definition to obtain a compound of the formula

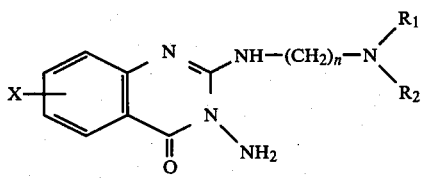

reacting the latter with a formylation agent to obtain the corresponding compound of formula I and optionally reacting the latter with a non-toxic, pharmaceutically acceptable acid to obtain the corresponding acid addition salt of the compound of formula I.

Examples of suitable halogens of X are fluorine, chlorine and bromine. Examples of R$_1$ and R$_2$ are hydrogen, alkyl of 1 to 5 carbon atoms such as methyl, ethyl, propyl, isopropyl, butyl, isobutyl, tert.-butyl and pentyl; and hydroxyalkyl of 1 to 5 carbon atoms such as hydroxymethyl, hydroxypropyl, hydroxybutyl, hydroxypentyl and especially hydroxyethyl. Examples of suitable saturated heterocycle of

are pyrrolidino, piperidino, morpholino and piperazino, each of which may be substituted with at least one member of the group consisting of hydroxy; alkyl of 1 to 5 carbon atoms such as methyl and ethyl; hydroxyalkyl of 1 to 5 carbon atoms such as hydroxyethyl; cycloalkyl of 3 to 6 carbon atoms such as cyclopropyl and cyclohexyl; formyl, acetyl, carbamoyl, thiocarbamoyl, mono- or dialkylcarbamoyl or thiocarbamoyl of 1 to 5 alkyl carbon atoms and alkylsulfonyl with 1 to 6 alkyl carbon atoms, alkoxycarbonyl of 2 to 6 carbon atoms such as methoxycarbonyl, ethoxycarbonyl, propoxycarbonyl, butoxycarbonyl and isobutoxycarbonyl and aryl such as phenyl.

Examples of suitable acids for the formation of the non-toxic, pharmaceutically acceptable acid addition salts are mineral acids such as hydrochloric acid, hydrobromic acid, hydriodic acid, nitric acid, sulfuric acid and phosphoric acid and organic acids such as acetic acid, formic acid, propionic acid, maleic acid, fumaric acid, succinic acid, tartaric acid, citric acid, oxalic acid, glyoxylic acid or aspartic acid, alkanesulfonic acids such as methanesulfonic acid or ethanesulfonic acid, arylsulfonic acids, such as benzenesulfonic acid or p-toluenesulfonic acid or arylcarboxylic acids, such as benzoic acid. Such acid addition salts may contain more than one acid moiety and, for example, dihydrochlorides may be obtained.

Among the preferred compounds of formula I are those wherein X is hydrogen, methyl or nitro, those wherein n is 3, 4, or 5 and those wherein

form a saturated heterocycle containing another heteroatom and optionally substituted with at least one member of the group consisting of hydroxy, cycloalkyl of 3 to 6 carbon atoms, alkoxycarbonyl of 2 to 6 carbon atoms, phenyl and halophenyl. Especially preferred compounds are wherein X is hydrogen or methyl and

forms a 4-phenylpiperazin-1-yl, 4-(chlorophenyl)-piperazine-1-yl or 4-(ethoxycarbonyl)-piperazin-1-yl radical, especially piperazin-1-yl optionally substituted on the second nitrogen atom.

Particularly preferred compounds obtained according to the invention are ethyl 4-[4-(1,5-dihydro-7-methyl-5-oxo-[1,2,4]-triazolo-[5,1,b]-quinazolin-1-yl-butyl]-piperazine-1-carboxylate and its non-toxic, pharmaceutically acceptable acid addition salts.

In a preferred mode of the process of the invention, the reaction of the compounds of formulae II and III is effected by heating to about 180° C. The formylation agent may be an alkyl orthoformate of 1 to 5 alkyl carbon atoms such as methyl orthoformate or ethyl orthoformate or formic acid or the dimethyl acetal or diethyl acetal of dimethylformamide or dimethylformamide associated with an acid chloride such as benzoyl chloride. The formylation is effected in the presence of an acid agent such as p-toluene sulfonic acid at reflux in an inert organic solvent such as toluene.

The amino group optionally present in the

group of the compound of formula IV is protected, for example, by a formyl group, acyl group or an alkoxy carbonyl group during the formylation reaction which then is followed by deblocking of the amino group. When the compounds of formula I possess the

in the form a substituted heterocycle, notably a carbamoyl, thiocarbamoyl or alkylsulfonyl, they are prepared from the corresponding unsubstituted compounds, after optional deblocking of protected amino groups, by known substitution methods.

The compounds of formula IV are novel and are an object of the invention.

The compounds of formula III may be prepared by reacting a compound of the formula

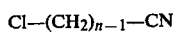

with a compound of the formula

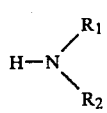

in toluene in the presence of triethylamine and reducing the resulting product with sodium borohydride in the presence of cobalt chloride in an alcohol such as methanol or by catalytic hydrogenation to obtain the compound of formula III. The catalytic hydrogenation may be effected in one or more steps and the reduction is preferably effected in the presence of acetic anhydride and hydrolysis of the acyl derivative.

In the following example there are described several preferred embodiments to illustrate the invention but it is to be understood that the invention is not intended to be limited to the specific embodiments.

EXAMPLE

Ethyl 4-[4-(1,5-dihydro-7-methyl-5-oxo-[1,2,4]-triazolo-[5,1-b]-quinazolin-1-yl-butyl]-piperazine-1-carboxylate STEP A: Ethyl 4-(3-cyclopropyl)-piperazine-1-carboxylate 124 g (1.2 M) of 4-chlorobutyronitrile were dissolved in 600 ml of toluene and the mixture was refluxed under a Dean-Stark separator for 1 hour. The resultant solution was cooled and then 158 g (1 M) of ethyl piperazine-1-carboxylate and 170 ml (1.2 M) of triethylamine were added thereto and the mixture was refluxed for 24 hours. The resulting suspension was cooled to 20° C. and one liter of ether was added thereto. The precipitate of triethylamine hydrochloride was filtered off and the filtrate was decolorized with charcoal and evaporated to dryness to obtain 200 g of ethyl 4-(3-cyclopropyl)-piperazine-1-carboxylate in the form of a brown oil which was distilled under reduced pressure at a boiling point of 140°-150° C. at 0.05 mm Hg.

STEP B: Ethyl 4-(4-aminobutyl)-piperazine-1-carboxylate (b₁) By Reduction With Cobaltous Chloride A solution of 200 g of ethyl 4-(3-cyanopropyl)-piperazine-1-carboxylate and 20 g of cobaltous chloride hexahydrate in 2 liters of methanol was cooled in ice and 125 g of sodium borohydride were added in portions with stirring at a temperature of less than 10° C. When the addition was complete, the mixture was stirred at 20° C. for 16 hours and then ~300 ml of concentrated HCl were added thereto until the black suspension turned blue. The solvent was removed under vacuum and the residue was dissolved in 2 liters of water and filtered. The filtrate was adjusted to a pH of 8 with potassium carbonate and was washed with 200 ml of carbon tetrachloride to remove non-polar impurities. The pH of the solution was increased to 9–10 by the addition of more potassium carbonate and then was saturated with sodium chloride. The mixture was extracted 6 times with 250 ml of chloroform and the combined extracts were dried over MgSO$_4$ and evaporated to dryness to obtain 30 g of ethyl 4-(4-aminobutyl)-piperazine-1-carboxylate in the form of a light brown oil which was distilled under reduced pressure to give a pure fraction with a boiling point of 135°–140° C. at 0.3 mm Hg.

(b$_2$) By One Step Catalytic Reduction 60 g of ethyl 4-(3-cyanopropyl)-piperazine-1-carboxylate were dissolved in a 10% w/w solution of ammonia in ethanol and 6 g of 5% rhodium on alumina were added thereto. The mixture was cooled to room temperature and filtered. The filtrate was evaporated to dryness under vacuum and the residual oil was distilled under reduced pressure to obtain 20 g of ethyl 4-(4-aminobutyl)-piperazine-1-carboxylate with a boiling point of 126°–130° C. at 0.15 to 0.2 mm Hg.

(b$_3$) By 2 Stage Catalytic Reduction (i) Ethyl 4-(4-acetamidobutyl)-piperazine-1-carboxylate 20 g-(wet weight) of Raney nickel T-1 were washed twice with acetic anhydride and then added to a solution of 100 g of ethyl 4-(3-cyanopropyl)-piperazine-1-carboxylate in 300 ml of acetic anhydride. 30 g of sodium acetate were added thereto and the mixture was hydrogenated at 4 atmospheres pressure at 50° C. until uptake of hydrogen ceased (approx. 2 hours). The mixture was cooled to room temperature and was poured into 600 ml of water. When the reaction had subsided (temperature rose to ~60° C.), the catalyst was filtered off and was washed with water. The filtrate was adjusted to a pH of 8–9 with ~250 g sodium hydroxide in 250 ml water and was filtered through 'celite' to remove nickel salts. The filter pad was washed thoroughly with water and chloroform and the filtrate was extracted twice with 500 ml of chloroform. The organic solution was dried over MgSO$_4$ and was evaporated to dryness. The residue was crystallized from ether to obtain 105 g (88% yield) of ethyl 4-(4-aminobutyl)-piperazine-1-carboxylate.

(ii) Ethyl 4-(4-aminobutyl)-piperazine-1-carboxylate 6 g of ethyl 4-(4-acetamidobutyl)-piperazine-1-carboxylate were dissolved in a mixture of 12 ml of conc. hydrochloric acid and 24 ml of water and the solution was refluxed for 5 hours. The solution was then cooled to room temperature and made alkaline with potassium carbonate. The mixture was extracted 3 times with 100 ml of chloroform and the combined extracts were dried over MgSO$_4$ and evaporated to dryness to obtain 4 g (79% yield) of ethyl 4-(4-aminobutyl)-piperazine-1-carboxylate in the form of a pale yellow oil which slowly solidified.

STEP C: Ethyl 4-[4-(3-amino-6-methyl-quinazolin-2-yl-amino)-butyl]-piperazine-1-carboxylate A mixture of 10 g of ethyl 4-(4-aminobutyl)-piperazine-1-carboxylate, 5 g of 3-amino-2-hydrazino-6-methylquinazolin-4-(3H)-one and 0.5 g of p-toluenesulfonic acid was heated to 180° C. (bath temperature of reaction mixture 160° C.) for 4 hours. After cooling to 100° C., the reaction mixture was dissolved in 250 ml of toluene and was washed twice with 100 ml of water. The mixture filtered through 'celite' and the product was retained in the toluene solution for use in the next stage.

STEP D: Ethyl 4-[4-(1,5-dihydro-7-methyl-5-oxo-[1,2,4]-triazolo-[5,1-b]-quinazolin-1-yl)-butyl]-piperazine-1-carboxylate 0.25 g of p-toluenesulfonic acid was added to the solution from Step C and the mixture was refluxed under a Dean-Stark separator for 30 minutes. The solution was cooled slightly and then 7.5 ml of ethyl orthoformate were added thereto. The mixture was refluxed for 20 hours and the solution was cooled and reduced in volume to 25 ml under vacuum. The residue was triturated with 200 ml of ether to obtain a buff crystalline solid which was filtered off, washed with ether and dried under vacuum to obtain 6.3 g of ethyl 4-[4-(1,5-dihydro-7-methyl-5-oxo-[1,2,4]-triazolo-[5,1-b]-quinazolin-1-yl)-butyl]-piperazine-1-carboxylate.

Various modifications of the compounds and process of the invention may be made without departing from the spirit or scope thereof and it is to be understood that the invention is intended to be limited only as defined in the appended claims.

What we claim is:

1. A process for the preparation of triazoloquinazolinones of the formula

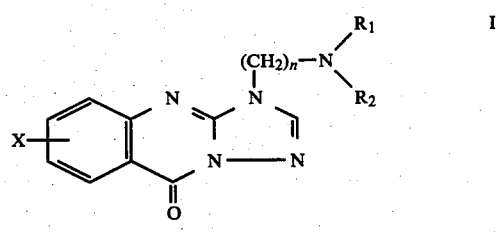

wherein X is selected from the group consisting of hydrogen, fluorine, chlorine, bromine, —NO$_2$, —CF$_3$, —CH$_3$ and —OCH$_3$, n is an integer from 2 to 5, R$_1$ and R$_2$ are individually selected from the group consisting of hydrogen, alkyl of 1 to 5 carbon atoms and hydroxyalkyl of 1 to 5 carbon atoms or taken together with the nitrogen atom which they are attached form a saturated heterocycle optionally containing another heteroatom and optionally substituted with at least one member of the group consisting of hydroxy, alkyl and hydroxy alkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms, phenyl and phenyl substituted with halogen or —CF$_3$ comprising reacting a compound of the formula

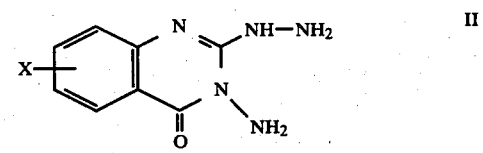

wherein X has the above definition with a compound of the formula

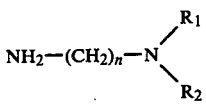 III wherein $R_1$, $R_2$ and n have the above definition to obtain a compound of the formula

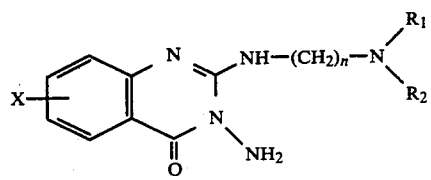 IV reacting the latter with a formylation agent to obtain the corresponding compound of formula I and optionally reacting the latter with a non-toxic, pharmaceutically acceptable acid to obtain the corresponding acid addition salt of the compound of formula I.

2. The process of claim 1 wherein

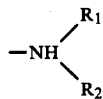

is piperazin-1-yl optionally substituted on the second nitrogen atom.

3. The process of claim 1 or 2 wherein the reaction of the compounds of formulae II and III is effected by heating at about 180° C.

4. The process of claim 1 or 2 wherein the formylation agent is selected from the group consisting of an alkyl orthoformate of 1 to 5 alkyl carbon atoms, formic acid, dimethyl and diethyl acetal of dimethylformamide and dimethylformamide associated with an acid chloride.

5. The process of claim 1 or 2 wherein the formylation is effected in the presence of an acid agent at reflux in an inert organic solvent.

6. The process of claim 1 wherein the formylation is effected in the presence of p-toluenesulfonic acid at reflux in toluene.

7. The process of claim 1 wherein the optional amino groups in

are protected during the formylation reaction and are then deblocked.

8. The method of claim 1 wherein

is a heterocycle substituted with a carbamoyl, thiocarbamoyl or alkylsulfonyl.

9. The process of claim 1 wherein $R_1$ and $R_2$ together with the nitrogen atom to which they are attached form a member of the group consisting of 4-phenylpiperazin-1-yl, 4-(chlorophenyl)-piperazine-1-yl or 4-(ethoxycarbonyl)-piperazin-1-yl radical and piperazin-1-yl optionally substituted on the second nitrogen atoms and optionally substituted with at least one member of the group consisting of hydroxy, alkyl and hydroxyalkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms, phenyl and phenyl substituted with halogen or —$CF_3$.

* * * * *

UNITED STATES PATENT AND TRADEMARK OFFICE
CERTIFICATE OF CORRECTION

PATENT NO. : 4,390,627
DATED : June 28, 1983
INVENTOR(S) : WILFRED R. TULLY

It is certified that error appears in the above-identified patent and that said Letters Patent is hereby corrected as shown below:

Column 4, line 60, "hex-" should read -- hexa- --.

Column 4, line 61, "ahydrate" should resd -- hydrate --.

Signed and Sealed this

Fifth Day of June 1984

[SEAL]

Attest:

GERALD J. MOSSINGHOFF

Attesting Officer    Commissioner of Patents and Trademarks